United States Patent
Shail

(10) Patent No.: US 8,984,844 B2
(45) Date of Patent: Mar. 24, 2015

(54) TABLET CONTAINER FILLING APPARATUS AND METHOD

(75) Inventor: Kenneth Shail, Malvern (GB)

(73) Assignee: Sparc Systems Limited, Malvern Worcestershire (GB)

(*) Notice: Subject to any disclaimer, the term of this patent is extended or adjusted under 35 U.S.C. 154(b) by 613 days.

(21) Appl. No.: 13/379,361

(22) PCT Filed: Sep. 14, 2010

(86) PCT No.: PCT/GB2010/051543
§ 371 (c)(1),
(2), (4) Date: Dec. 20, 2011

(87) PCT Pub. No.: WO2011/007186
PCT Pub. Date: Jan. 20, 2011

(65) Prior Publication Data
US 2012/0096816 A1    Apr. 26, 2012

(30) Foreign Application Priority Data
Jul. 15, 2009 (GB) .................................. 0912262.3

(51) Int. Cl.
*B65B 3/26* (2006.01)
*B65B 5/10* (2006.01)
*B65B 57/14* (2006.01)
(Continued)

(52) U.S. Cl.
CPC .............. *B65B 5/103* (2013.01); *B65B 57/14* (2013.01); *B65B 57/20* (2013.01); *G01N 21/9508* (2013.01)
USPC ................ 53/54; 53/473; 53/493; 356/402

(58) Field of Classification Search
CPC .......................................................... B65B 3/26
USPC ................ 53/473, 54; 356/402; 250/226
See application file for complete search history.

(56) References Cited

U.S. PATENT DOCUMENTS

| 4,878,336 A | 11/1989 | Kohler |
| 5,021,645 A | 6/1991 | Satula et al. |
| 6,191,859 B1 * | 2/2001 | Winterbottom et al. ...... 356/406 |

(Continued)

FOREIGN PATENT DOCUMENTS

| JP | 04305280 | 10/1992 |
| JP | 2004115128 | 4/2004 |

(Continued)

OTHER PUBLICATIONS

British Search Report dated Jan. 4, 2011 for BG0912262.3 (priority application).

(Continued)

*Primary Examiner* — Michelle Lopez
(74) *Attorney, Agent, or Firm* — Fleit Gibbons Gutman Bongini & Bianco PL; Paul D. Bianco; Martin Fleit

(57) ABSTRACT

Tablet-container filling apparatus is provided for feeding and separating tablets and for filling a tablet container with the said tablets. The tablet-container filling apparatus comprises a tablet-color identifier (3, 5), a tablet remover (4) whereby a rogue tablet is removable once identified by the tablet-color identifier, a tablet counter (7), a container conveyor (9), and a controller (5, 7) for controlling tablet flow into a container on said conveyor, the tablet-color identifier (3, 5) being on at least two sides of a tablet flow path, so that in use a tablet color is identifiable from at least said two sides.

19 Claims, 4 Drawing Sheets

(51) Int. Cl.
   *B65B 57/20* (2006.01)
   *G01N 21/95* (2006.01)

(56) References Cited

U.S. PATENT DOCUMENTS

| | | |
|---|---|---|
| 6,378,572 B1 | 4/2002 | Neubauer et al. |
| 7,339,660 B1 | 3/2008 | Cohn et al. |
| 2009/0056825 A1 | 3/2009 | Mertens et al. |

FOREIGN PATENT DOCUMENTS

| | | |
|---|---|---|
| JP | 2005315574 | 10/2005 |
| JP | 2009050760 | 3/2008 |
| JP | 2010042326 | 2/2010 |

OTHER PUBLICATIONS

International Search Report dated Jan. 17, 2011 for PCT/GB10/51543.
Written Opinion dated 2011 for PCT/GB10/51543.

* cited by examiner

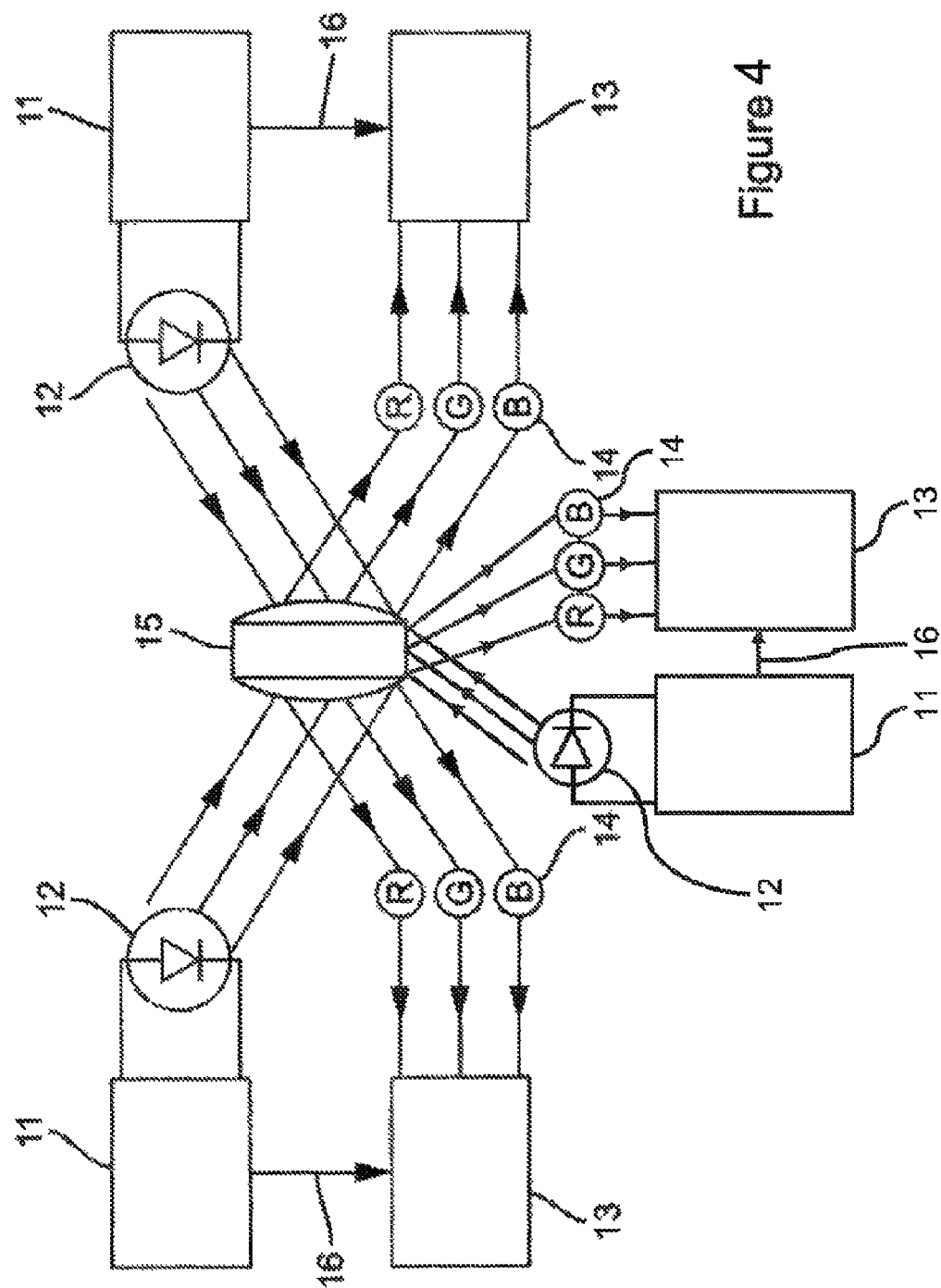

TABLET CONTAINER FILLING APPARATUS AND METHOD

FIELD OF THE INVENTION

The present invention relates to tablet-container filling apparatus, and to a method of identifying tablet colour.

BACKGROUND OF THE INVENTION

A system is required for the colour inspection of pharmaceutical tablets while they are being automatically counted into containers. When filling containers with pharmaceutical tablets, the tablets must be inspected for the correct colour, as the colour is an indication of their active ingredient or dose. The actual colour used in any particular situation is manufacturer dependent.

Since a rogue tablet could typically be left un-noticed on a ledge from a previous use of the filling apparatus when a different tablet was being filled into containers, the most effective point at which to inspect tablets in the filling process should be as close to their entry point to the container, typically a bottle or plastic container, as possible.

It is known that a typical filling machine has apparatus for separating the tablets in to a single-file, termed as "singulating", and then counting the tablets as they pass through a sensing device on their way into the container. When the required number of tablets has entered the container, a mechanism intercepts the flow while the container is replaced by the next empty one.

Such a machine often has a multiplicity of such singulating, sensing and intercepting devices working in parallel, in order to increase the overall rate of filling.

Conventional colour-sensing cameras are often mounted above the singulating device, for example, being a vibrating tray having multiple V shaped channels, with each channel transporting one row of tablets.

US Patent Application US2009/0056825A1 discloses the use of a vision system mounted above the product whilst it is on the singulating device.

These known systems have the following shortcomings.

The vision system is only capable of determining the colour of the aspect of the tablet that is nearest to them. One aspect of the tablet is hidden against the singulating device.

This is particularly pertinent when considering bi-layer tablets which are usually two colours, for example top blue and bottom white, and which are increasingly common in the pharmaceutical industry.

While a vision system could be set so as to accept blue and/or white tablets it could not detect the most common manufacturing defect of bi-layer tablets, being de-lamination. This system would consider a de-laminated or half thickness tablet as one blue and one white product.

The arrangement and mounting of the vision system does not allow it to inspect at a sufficiently late position in the process.

High levels of illumination are required. Such illumination dictates that covers are used to prevent eye-damage to the user. The covers are also required to eliminate the effects of ambient lighting. The covers cause difficulty in cleaning the machinery.

SUMMARY OF THE INVENTION

The present invention seeks to provide a solution to these problems.

According to a first aspect of the invention, there is provided tablet-container filling apparatus for feeding and separating tablets and for filling a tablet container with the said tablets, the tablet-container filling apparatus comprising a tablet-colour identifier, a tablet remover whereby a rogue tablet is removable once identified by the tablet-colour identifier, a tablet counter, a container conveyor, and a controller for controlling tablet flow into a tablet container on said conveyor, the tablet-colour identifier being on at least two sides of a tablet flow path, so that in use a tablet colour is identifiable from at least said two sides.

Preferable and/or optional features of the invention are set forth in claims 2 to 19, inclusive.

According to a second aspect of the invention, there is provided a method of identifying tablet colour using tablet-container filling apparatus in accordance with the first aspect of the invention, the method comprising the step of feeding a tablet onto a vertical tablet flow path, and providing tablet-colour recognition means on at least two sides of the vertical tablet flow path so that a colour of the tablet is determined from at least two different directions.

BRIEF DESCRIPTION OF THE DRAWINGS

The invention will now be more particularly described, by way of example only, with reference to the accompanying drawings, in which:

FIG. 4 is a diagrammatic view of an embodiment of a tablet-colour identifier with emitter/receivers positioned to detect three sides of the product.

DETAILED DESCRIPTION OF THE INVENTION

Figure 1:
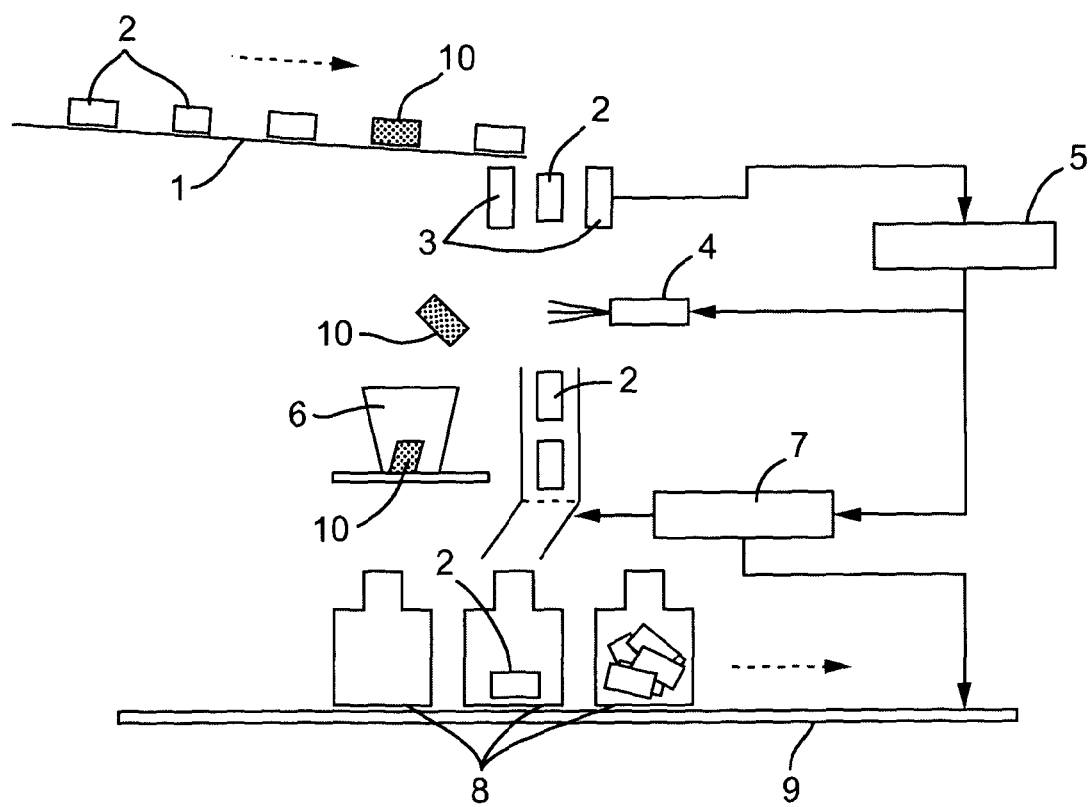
FIG. 1 is a diagrammatic overview of one embodiment of tablet-container filling apparatus, in accordance with the first aspect of the invention.

FIG. 1 shows an embodiment of a tablet-container filling apparatus where a feed device 1 feeds and separates tablets 2 which then free fall through optical or Electrostatic Field Sensors (EFS) 3. A controller, including a process control unit 5, activates a tablet remover, such as a reject ejector device 4, if a rogue tablet 10 is identified. The rogue tablet 10 is thus extracted from the tablet flow path and enters a reject container 6. The reject ejector device 4 may be mechanical or high speed pneumatic as shown in FIG. 1. Additionally or alternatively, an alarm signal and machine stop output can be activated.

A tablet counter being part of an index control unit 7 of the controller counts the number of good tablets 2 falling down into containers 8 such that the flow is interrupted by the controller when the requisite quantity has been counted, and the next empty container 8 is moved into position. The containers 8 are moved along a conveyor 9 beneath the index control unit 7.

The process control system 5 can comprise one of two systems or a combination of the two systems. In the first system, the tablets are counted by a microcomputer provided in the process control system that takes impulses from a set of optical, typically infrared, transmitters which form a grid of light-beams through which the tablets fall. The tablet is always guaranteed to break at least one beam irrespective of its lateral position.

In the second system, which is an alternative or additional system to that described above, an Electrostatic Field Sensor may be used. This enables the tablets to be sensed as they fall through a generated electrostatic field and a measure of their physical size to be made by way of the perturbation they make to the electrostatic field.

The tablet-colour identifier of the invention utilises tablet-colour recognition means comprising an RGB system which incorporates a set of light-emitting diodes for illuminating the tablets from at least two sides while they are in free-fall along a vertical portion of the tablet flow path into the container 8, positioned very close to the aforementioned systems. A corresponding set of colour sensors, such as colour sensing semiconductors or photoreceptors, measure the reflected light.

The RGB system could be used to perform the same function as any optical sensing means that is already known.

The illuminating diodes can be those which emit broad spectrum light comprising approximately equal red, green and blue energy together with separate colour sensing semiconductor devices, one corresponding to each colour.

OR

A separate set of illuminating devices for each primary colour red, green, blue can be used with one set of wideband sensors in which the red, green and blue illuminators are sequentially energised. The synchronising circuits are the arranged to separate the received signals according to which colour is energised at any part of the cycle.

In both implementations the transmitting devices can be pulsed at much higher current levels than their maximum rated current at low duty cycles thereby producing much higher output power for a short part of their repetitive sequence.

Figure 2:
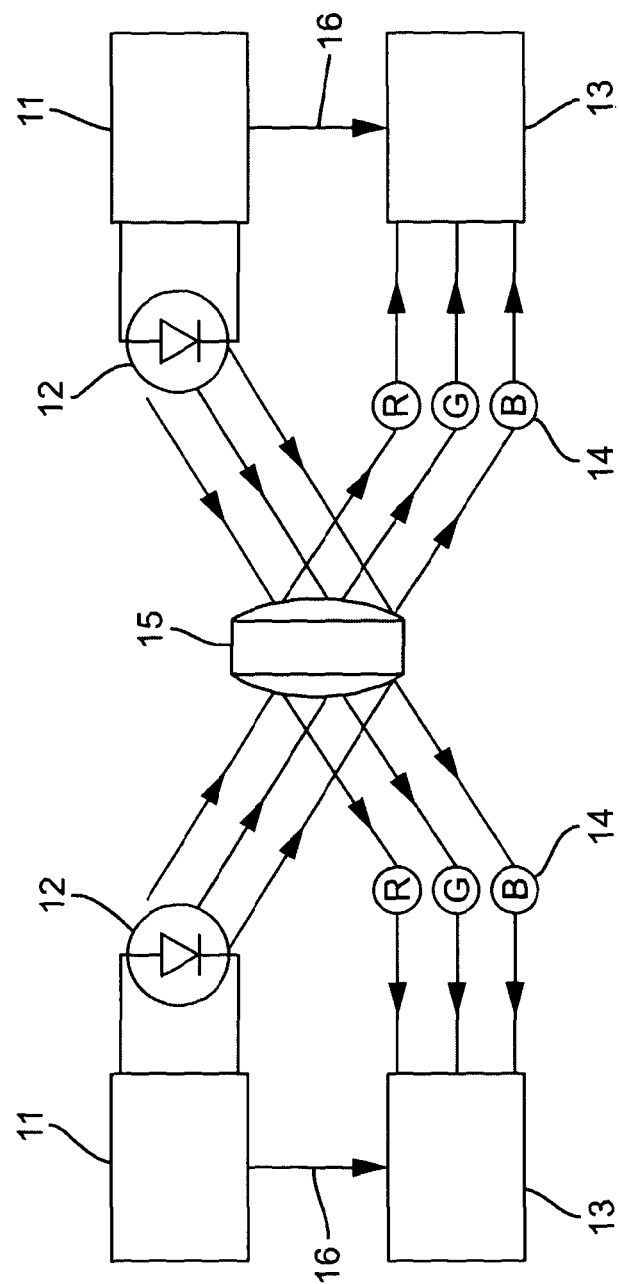
FIG. 2 is a diagrammatic view of a first embodiment of a tablet-colour identifier of the apparatus shown in FIG. 1.

The first embodiment of the tablet-colour identifier is shown in FIG. 2, where a pulsed drive 11 powers a white light transmitter 12, which illuminates a tablet 15 falling along a vertical tablet flow path. The tablet 15 may be a solid, a capsule, a soft gel, or any such form that the item may take. The light reflected from the tablet 15 falls upon three narrow spectrum receivers, being red, green and blue 14. One of each receiver 14, or a plurality of each receiver 14 may be provided. There may also be different numbers of the different receivers 14. There is a synchronization signal 16 between the pulsed drive 11 and signal processor 13.

The emitter/receivers will be positioned to detect either two sides of the product as illustrated in FIG. 2, or four sides of the product, if each arrangement is replicated four times. Other numbers of emitters/receivers can be considered, such as three, or more than four. FIG. 4 shows an embodiment of a tablet-colour identifier with emitter/receivers positioned to detect three sides of the product. Preferably, at least a majority of a lateral perimeter of the vertical tablet flow path is surrounded by the emitters and receivers.

Figure 3:
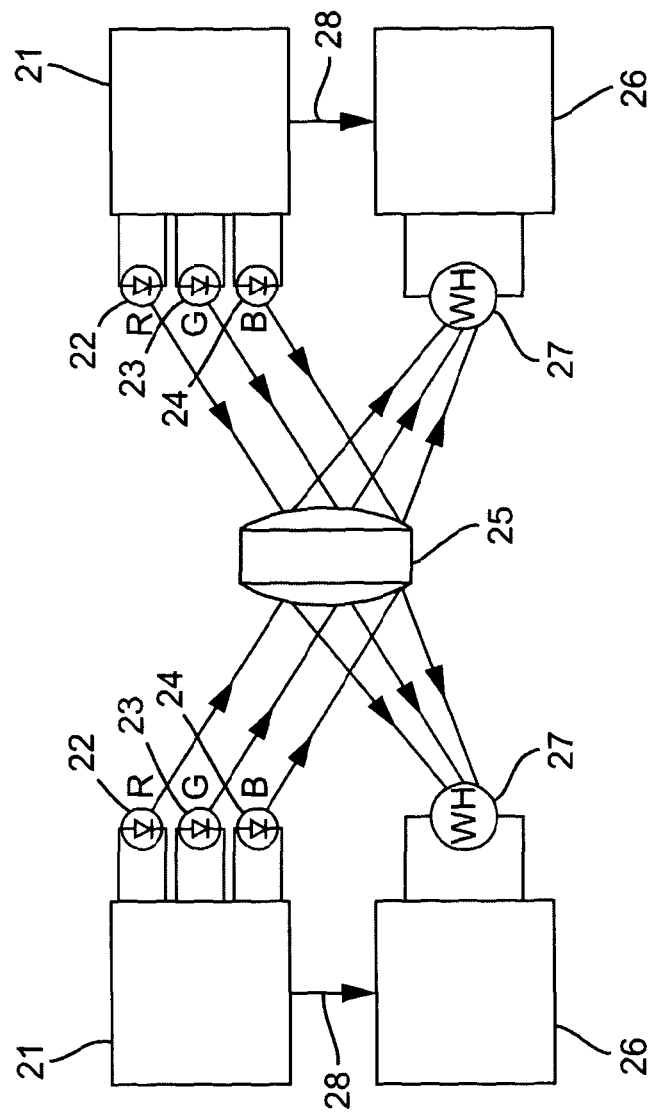
FIG. 3 is a diagrammatic view of a second embodiment of a tablet-colour identifier of the apparatus shown in FIG. 1.

Referring to FIG. 3, a second embodiment of the additional colour detecting system is shown. In this case, a pulsed drive 21 provides sequential drive pulses, red, green and blue, to three light emitting diodes, being red 22, green 23 and blue 24.

The light thus emitted falls upon the tablet 25 and is reflected to fall upon a broad spectrum receiver 27, which detects the sequentially reflected red, green and blue light, and the output of the receiver 27 is fed to a signal processor 26.

There is a Synchronization signal 28 between the pulsed drive 21 and signal processor 26.

The emitter/receivers will be positioned to detect either two sides of the product as illustrated in FIG. 3, or four sides of the product, if each arrangement is replicated four times. As above, other numbers of emitters/receivers can be considered, such as three, or more than four. Preferably, at least a majority of a lateral perimeter of the vertical tablet flow path is surrounded by the emitters and receivers.

There can be multiple replications of items 11, 12, 13, 14 & 16 in FIG. 2, or 21, 22, 23, 24, 26, 27 & 28 in FIG. 3, depending on the method used, per side to enable maximum illumination and reception of light over an aperture which is considerably larger than the tablet. Such an arrangement will allow tablets to fall through different parts of the aperture and always have their colour sensed, regardless of their actual lateral trajectory.

Although the primary RGB colours are preferably utilised, other colours, for example, secondary colours, could be considered either alone or in combination with the RGB colours.

The tablet-colour identifier is a tablet-colour identification element, module, unit or device within the apparatus. The tablet remover is a tablet removal element, module, unit or device within the apparatus. The apparatus may also be considered to be a system, and is intended to cover such.

The above arrangement of the RGB system, because it is monitoring the colour ratio, would be able to, for example, determine that the tablet is blue and white, or just white or just blue. Additionally, although the vibratory feed mechanism that delivers the tablets is intended to present the product singularly, this cannot be guaranteed, and while a camera based system could not "see" a tablet hidden behind another tablet, the EFS sensor mentioned above can detect this condition. Therefore, if two bi-layer tablets pass through the RGB system together, with their blue sides facing each other, and the RGB system could only detect the predominance of white, the EFS sensor result would disagree with the RGB sensor result when both results are compared; the net result would be a "mismatch" and the tablets would be rejected.

It is thus possible to provide tablet-container filling apparatus which includes a tablet-colour identifier for identifying the colour of a tablet from at least two different sides. The apparatus is positioned as closely as possible to the container being filled to prevent or limit any possibility of a rogue tablet entering the container. The apparatus does not require expensive vision systems utilising cameras, and thus reduces installation and operation costs. Light glare is also reduced, and thus covers can be dispensed with.

The embodiments described above are provided by way of examples only, and various other modifications will be apparent to persons skilled in the art without departing from the scope of the invention as defined by the appended claims.

The invention claimed is:

1. Tablet-container filling apparatus for feeding and separating tablets and for filling a tablet container with the said tablets, the tablet-container filling apparatus comprising a tablet-colour identifier, a tablet remover whereby a rogue tablet is removable once identified by the tablet-colour identifier, a tablet counter, a container conveyor, and a controller which controls tablet flow into a tablet container on said conveyor, wherein the tablet-colour identifier is on at least two sides of a tablet flow path, so that in use a tablet colour is identifiable from at least said two sides, wherein the tablet-colour identifier includes a plurality of electromagnetic radiation transmitters arranged to output a grid of electromagnetic radiation through which a tablet passes so that, in use, the passing tablet is countable by the tablet counter.

2. Tablet-container filling apparatus as claimed in claim 1, wherein the tablet-colour identifier includes a plurality of light emitting elements arranged on at least two sides of the tablet flow path which outputs light beams incident with the flow path, wherein a tablet on the flow path is illuminable on at least two of its sides.

3. Tablet-container filling apparatus as claimed in claim 2, wherein the light emitting elements are light emitting diodes.

4. Tablet-container filling apparatus as claimed in claim 1, wherein the light emitting elements output broad spectrum light comprising at least red, green and blue light wavelengths.

5. Tablet-container filling apparatus as claimed in claim 4, wherein the tablet-colour identifier further includes a plurality of colour sensing semiconductor devices which receive reflected light from the light emitting elements, each colour sensing semiconductor device corresponding to one of the said at least red, green and blue wavelengths.

6. Tablet-container filling apparatus as claimed in claim 1, wherein each said light emitting element can output one of red, green and blue light.

7. Tablet-container filling apparatus as claimed in claim 6, wherein an equal number of said light emitting elements are provided for each colour light.

8. Tablet-container filling apparatus as claimed in claim 6, wherein the controller is adapted to sequentially energise the different coloured light emitting elements.

9. Tablet-container filling apparatus as claimed in claim 6, wherein the tablet-colour identifier further includes a plurality of colour sensing semiconductor devices which receive reflected light from the light emitting elements, each colour sensing semiconductor device corresponding to one of the said at least red, green and blue wavelengths.

10. Tablet-container filling apparatus as claimed in claim 9, wherein the controller is adapted to sequentially energise the different colour sensing semiconductor devices.

11. Tablet-container filling apparatus as claimed in claim 1, wherein the transmitters are infra-red transmitters.

12. Tablet-container filling apparatus as claimed in claim 1, wherein the tablet-colour identifier includes an electrostatic field sensor which senses a physical size of a tablet passing thereby due to perturbation of an emitted electrostatic field.

13. Tablet-container filling apparatus as claimed in claim 1, wherein the tablet-colour identifier is spaced above the tablet remover whereby the tablet flow path therebetween is vertical or substantially vertical, the tablet-colour identifier being at a lateral perimeter of the tablet flow path.

14. Tablet-container filling apparatus as claimed in claim 13, wherein the tablet-colour identifier is on at least three sides of the tablet flow path.

15. Tablet-container filling apparatus as claimed in claim 13, wherein the tablet-colour identifier at least substantially surrounds a lateral perimeter of the tablet flow path.

16. Tablet-container filling apparatus as claimed in claim 13, wherein the tablet flow path between at least the tablet-colour identifier and the tablet remover is gravity-assisted.

17. Tablet-container filling apparatus as claimed in claim 1, wherein the tablet remover includes a gas discharge device for blowing a rejected tablet onto a secondary flow path to a rejected tablet container.

18. A method of identifying tablet colour using tablet-container filling apparatus, the method comprising the step of feeding a tablet onto a vertical tablet flow path, and providing a tablet-colour identifier on at least two sides of the vertical tablet flow path so that a colour of the tablet is determined from at least two different directions.

19. A method as claimed in claim 18, further comprising a subsequent step of blowing the tablet off the said vertical flow path if the colour recognised by the tablet-colour identifier does not correspond to an expected colour.

\* \* \* \* \*